(12) United States Patent
Suzuki et al.

(10) Patent No.: US 8,715,639 B2
(45) Date of Patent: May 6, 2014

(54) COMPOSITIONS AND METHODS FOR MICROBE STORAGE AND DELIVERY

(75) Inventors: Hideki Suzuki, Madison, WI (US); Salvatore Braico, Madison, WI (US)

(73) Assignee: Conjugon, Inc., Madison, WI (US)

( * ) Notice: Subject to any disclaimer, the term of this patent is extended or adjusted under 35 U.S.C. 154(b) by 732 days.

(21) Appl. No.: 12/671,370

(22) PCT Filed: Sep. 7, 2007

(86) PCT No.: PCT/US2007/019520
§ 371 (c)(1), (2), (4) Date: Jan. 29, 2010

(87) PCT Pub. No.: WO2009/020455
PCT Pub. Date: Feb. 12, 2009

(65) Prior Publication Data
US 2011/0020307 A1   Jan. 27, 2011

Related U.S. Application Data

(63) Continuation of application No. 11/836,021, filed on Aug. 8, 2007, now abandoned.

(51) Int. Cl.
*A61K 9/00* (2006.01)
*A01N 63/00* (2006.01)
*A01N 65/00* (2009.01)
*C12N 1/00* (2006.01)
*C12N 1/04* (2006.01)
*C12N 1/12* (2006.01)
*C12N 1/20* (2006.01)
*C12N 1/22* (2006.01)
*C12N 11/04* (2006.01)
*C12N 11/08* (2006.01)
*C12N 11/12* (2006.01)
*C12P 1/00* (2006.01)

(52) U.S. Cl.
USPC ............ 424/93.1; 424/400; 435/41; 435/179; 435/180; 435/182; 435/243; 435/252; 435/252.1; 435/252.8; 435/260; 435/849

(58) Field of Classification Search
None
See application file for complete search history.

(56) References Cited

U.S. PATENT DOCUMENTS

| | | | |
|---|---|---|---|
| 4,442,133 A | 4/1984 | Greco et al. | |
| 4,642,104 A | 2/1987 | Sakamoto | |
| 5,089,205 A | 2/1992 | Huang et al. | |
| 5,217,493 A | 6/1993 | Raad et al. | |
| 5,498,416 A | 3/1996 | Carsenti-Etesse et al. | |
| 5,616,338 A | 4/1997 | Fox et al. | |
| 5,624,704 A | 4/1997 | Darouiche et al. | |
| 5,645,830 A | 7/1997 | Reid | |
| 5,705,160 A | 1/1998 | Bruce et al. | |
| 5,709,857 A | 1/1998 | Morelli et al. | |
| 5,716,406 A | 2/1998 | Farber | |
| 5,804,179 A | 9/1998 | Bruce et al. | |
| 5,853,745 A | 12/1998 | Darouiche | |
| 5,902,283 A | 5/1999 | Darouiche et al. | |
| 6,004,551 A | 12/1999 | Reid et al. | |
| 6,143,037 A | 11/2000 | Goldstein et al. | |
| 6,162,487 A | 12/2000 | Darouiche | |
| 6,166,007 A | 12/2000 | Sodemann | |
| 6,296,863 B1 | 10/2001 | Trogolo et al. | |
| 6,365,220 B1 | 4/2002 | Burrell et al. | |
| 6,368,611 B1 | 4/2002 | Whitbourne et al. | |
| 6,423,706 B2 | 7/2002 | Sodemann | |
| 6,428,491 B1 | 8/2002 | Weiss | |
| 6,468,649 B1 | 10/2002 | Zhong | |
| 6,498,157 B2 | 12/2002 | Sodemann | |
| 6,558,686 B1 | 5/2003 | Darouiche | |
| 6,589,591 B1 | 7/2003 | Mansouri et al. | |
| 6,719,991 B2 | 4/2004 | Darouiche et al. | |
| 6,918,927 B2 | 7/2005 | Bates et al. | |
| 2002/0120333 A1 | 8/2002 | Keogh et al. | |
| 2004/0166102 A1 | 8/2004 | Darouiche et al. | |
| 2005/0163757 A1 | 7/2005 | Filutowicz | |
| 2006/0159745 A1 | 7/2006 | Baksh | |
| 2006/0270040 A1 | 11/2006 | Filutowicz | |
| 2006/0270044 A1 | 11/2006 | Suzuki | |

FOREIGN PATENT DOCUMENTS

| | | |
|---|---|---|
| FR | 2874826 | 3/2006 |
| GB | 2261372 | 5/1993 |
| GB | 2331717 | * 6/1999 |
| WO | WO00/16624 | 3/2000 |
| WO | 0195876 | * 12/2001 |
| WO | 2005034861 | 4/2005 |
| WO | 2009020455 | 2/2009 |

OTHER PUBLICATIONS

Andersson, et al. "Persistence of *Escherichia coli* bacteriuria is not determined by bacterial adherence" Infect Immun. Sep. 1991;59(9):2915-21.

Brook "Bacterial Interference" Critical Reviews in Microbiology, 25(3): 155-172 (1999).

Darouiche, et al. "Antibiotic penetration of and bactericidal activity within endothelial cells" Antimicrobial Agents & Chemotherapy 38/5: 1059-1064, May 1994.

Darouiche, et al. "Vancomycin penetration into biofilm covering infected prostheses and effect on bacteria" J Infect Dis. Sep. 1994;170(3):720-3.

Finegold, et al. "General Principle in Staining Procedures" Diagnostic Microbiology, 6th Ed., CV Mosby St. Louis, pp. 13-15 (1982).

Hull, et al. "Role of type 1 fimbria- and P fimbria-specific adherence in colonization of the neurogenic human bladder by *Escherichia coli*" Infect Immun. Nov. 2002; 70(11):6481-4.

(Continued)

*Primary Examiner* — Debbie K Ware
(74) *Attorney, Agent, or Firm* — Casimir Jones S.C.

(57) ABSTRACT

The present invention relates to the field of bacteriology. In particular, the invention relates to compositions of probiotic microbes and methods for making and using such compositions, e.g. in the treatment and prevention of catheter associated urinary tract infections.

25 Claims, 1 Drawing Sheet

(56) References Cited

OTHER PUBLICATIONS

Hull, et al. "Urinary Tract Infection Prophylaxis Using *Escherichia coli* 83972 in Spinal Cord Injured Patients" The Journal of Urology, vol. 163, 872-877, Mar. 2000.

Hull, et al. "Virulence Properties of *Escherichia coli* 83972, a Prototype Strain Associated with Asymptomatic Bacteriuria" Infection and Immunity, Jan. 1999, p. 429-432.

Maki, et al. "Engineering out the risk for infection with urinary catheters" Emerg Infect Dis. Mar.-Apr. 2001; 7(2):342-7.

Nicolle "Catheter-related urinary tract infection" Drugs Aging. 2005;22(8):627-39.

Nidrr "The prevention and management of urinary tract infections among people with spinal cord injuries" Journal of the American Paraplegia Society, vol. 15, No. 3, pp. 194-204, Jul. 1992.

Raad, et al. "Antibiotics and prevention of microbial colonization of catheters" Antimicrob Agents Chemother. Nov. 1995, vol. 39(11), pp. 2397-2400.

Reid, et al. "Is there a role for lactobacilli in prevention of urogenital and intestinal infections?" Clinical Microbiology Reviews, Oct. 1990, 3(4):335-344.

Reid, et al. "Potential uses of probiotics in clinical practice" Clin Microbiol Rev. Oct. 2003;16(4):658-72.

Roos, et al. "The asymptomatic bacteriuria *Escherichia coli* strain 83972 outcompetes uropathogenic *E. coli* strains in human urine" Infect Immun. Jan. 2006;74(1) pp. 615-624.

Rupp, et al. "Effect of silver-coated urinary catheters: efficacy, cost-effectiveness, and antimicrobial resistance" Am J Infect Control. Dec. 2004;32(8):445-50.

Solomon, et al. "Partial correlation of distance matrices in studies of population structure" Antibiotic Releasing Polymers; Journal of Controlled Release, 6 (1987) 343-352.

Srinivasan, et al. "A prospective trial of a novel, silicone-based, silver-coated foley catheter for the prevention of nosocomial urinary tract infections" Infect Control Hosp Epidemiol. Jan. 2006;27(1):38-43.

Trautner, et al. "*Escherichia coli* 83972 Inhibits Catheter Adherence by a Broad Spectrum of Uropathogens" Urology. 61(5):1059-1062; 2003.

Trautner, et al. "Pre-Inoculation of Urinary Catheters with *Escherichia coli* 83972 Inhibits Catheter Colonization by *Enterococcus faecalis*" The Journal of Urology, 167:375-379 (Jan. 2002).

Trautner, et al., "Coating Urinary Catheters with an Avirulent Strain of *Escherichia coli* as a Means to Establish Asymptomatic Colonization." Infect Control Hosp Epidemiol. Jan. 2007;28(1):92-94.

Wong, et al. "Guideline for prevention of catheter-associated urinary tract infections." Center for Disease Control and Prevention (1981).

English Abstract of FR 2874826, published Mar. 10, 2006, as accessed from http://worldwide.espacenet.com on Aug. 14, 2012.

* cited by examiner

COMPOSITIONS AND METHODS FOR MICROBE STORAGE AND DELIVERY

FIELD OF THE INVENTION

The present invention relates to the field of bacteriology and probiotic therapies. In particular, the invention relates to novel compositions (e.g., probiotic microbe preparations) and methods of using the same (e.g., for coating surfaces, such as catheters). In some embodiments, the present invention comprises a freeze-dried composition comprising a microbe that can be reconstituted to form a gel, e.g., a medical lubricant, containing viable, colonogenic microbes.

BACKGROUND OF THE INVENTION

Bacteriuria and pyuria are uniformly present in patients who have indwelling urinary catheters. Antimicrobial therapy may transiently eradicate the bacteria, but bacteriuria promptly recurs, and the infecting bacteria become progressively resistant to antibiotics. No mode of treatment is known to eliminate chronic, subclinical infections or to prevent intercurrent, clinically important infections.

Universal guidelines intended to prevent or delay catheter-associated urinary tract infections (CAUTI) include the following: avoidance of unnecessary catheterization; use of a trained professional to insert and care for the catheter; prompt removal of the catheter when no longer needed; maintenance of sterile closed drainage; maintenance of good drainage; minimal manipulation of the system; use of a condom or suprapubic catheter instead of a urethral catheter; and separation of catheterized patients (NIDRR, "*SCI Nurs* 10(2): 49-61 Jan. 27-29, 1992; Maki, D. G. and P. A. Tambyah, *Emerg Infect Dis* 7(2): 342-7(2001)) from both each other and other patients in the hospital. Most measures that have been tested have not shown effectiveness in randomized clinical trials, however, and some are not applicable to patients with a neurogenic bladder.

Technologies have been tested for prevention of CAUTI, including use of anti-infective lubricants when inserting the catheter, use of sealed catheter-collection tubing junctions or anti-reflux valves, continuous irrigation of the catheterized bladder with an anti-infective solution through a triple lumen catheter, and periodic instillation of an anti-infective solution into the collection bag. However, these technologies have not been confirmed to be effective in randomized clinical trials (Maki and Tambyah, supra).

The use of anti-infective catheter material to reduce the incidence of CAUTI is under investigation. Catheters impregnated with antimicrobial agents may have some benefit, although studies have been small (Maki and Tambyah, supra). Silver-oxide coated catheters did not show efficacy in large randomized trials, and tests of the ability of a silver alloy hydrogel catheter to decrease infection produced conflicting trial results (Wong, E. and T. Hooton, "Guideline for prevention of catheter-associated urinary tract infections." *Center for Disease Control and Prevention* (1981); Rupp, M. E., T. Fitzgerald, et al., *Am J Infect Control* 32(8): 445-50 (2004).

Antimicrobial (e.g., antibiotic and/or antiseptic) treatment of asymptomatic urinary tract infections (UTI) in catheterized patients has not been shown to be of benefit, as treated and untreated catheterized patients have a similar prevalence of infection a few weeks after the end of treatment, and an equal likelihood of developing symptomatic episodes of UTI (Nicolle, L. E., *Drugs Aging* 22(8): 627-39 (2005). Additionally, antimicrobial treatment of asymptomatic CAUTI has been associated with the emergence of drug-resistant organisms, complicating management when a symptomatic infection does occur.

Given the difficulty of eradicating bacteriuria in a patient with long-term bladder catheterization, the problem of chronic bacteriuria and recurrent UTI in catheter-dependent persons is not likely to be resolved by the use of antimicrobial agents. Studies have indicated that pre-colonization of the bladder with certain non-pathogenic strains of *E. coli* is a safe and effective way of preventing or reducing the in vitro incidence of urinary catheter colonization by a wide variety of uropathogens.

*Escherichia coli* 83972 is a clinical isolate associated with asymptomatic bacteriuria (Andersson et al., 1991, Infect. Immun. 59:2915-2921) and the strain has been used to successfully colonize bladders of human volunteers. *E. coli* HU2117, a variant of 83972 having a deleted papG83972 gene, has also been shown to successfully colonize the bladders of human subjects (Hull, et al., 2002, Infection and Immunity, 70(11):6481-6481).

However, existing methods of pre-inoculation of the urinary tract are cumbersome. In some instances, pre-colonization is accomplished by introducing a liquid preparation of bacteria directly into the bladder. Using this approach, the patient is first treated with appropriate antibiotics to sterilize the urine. After an antibiotic-free interval, the patient is catheterized and the bladder is emptied. Thirty milliliters of *E. coli* 83972 ($10^5$ colony-forming units (CFU)/mL) is instilled in the bladder and the catheter is removed. The procedure is repeated once daily for 3 days. According to individual study protocols, subsequent urine samples are taken to assess host response parameters, and to prove the success or failure of the colonization procedure.

Other groups have investigated pre-colonization by incubating the catheter itself in a broth containing the non-pathogenic microbe. For example, in published protocols, a catheter is immersed in a bacterial suspension for 48 hours to form a biofilm on the catheter. The resulting biofilms generally contain $5 \times 10^4$ to $1 \times 10^5$ colony forming units (cfu) of *E. coli* 83972 per centimeter of catheter tubing. The catheter is then inserted using conventional catheter lubrication (such as SteriLub lubricant, SurgiLube lubricant, KY Jelly) prior to insertion. It is believed that the biofilm on the catheter acts as a reservoir that can help keep the bladder colonized.

Such methods of delivering a probiotic to the bladder require physicians and hospitals to develop new procedures for the growth and administration of the microbes, and for the handling and use of catheters. There remains a need for improved methods and formulations for delivery of probiotic microbes to a subject. There also remains a need for improved methods of producing and using such formulations.

SUMMARY OF THE INVENTION

The present invention relates to the field of bacteriology and probiotic therapies. In particular, the invention relates to novel compositions (e.g., probiotic microbe preparations) and methods of using the same (e.g., for coating surfaces, such as catheters). In some embodiments, the present invention provides a composition comprising a probiotic microbe, a pharmaceutically acceptable gelling agent, and a pharmaceutically acceptable first protective agent, in freeze-dried form. In some embodiments, the composition further comprises a pharmaceutically acceptable second protective agent. In some embodiments, a single agent acts as both a gelling agent and a protective agent.

The invention is not limited to a particular probiotic microbe. In some embodiments of the present invention, the probiotic microbe comprises a strain of E. coli. In some preferred embodiments, the strain of E. coli is E. coli 83972, while in some preferred embodiments, the strain is E. coli HU2117.

The present invention contemplates a gelling agent but is not limited to any particular gelling agent. In some embodiments, the gelling agent is a pharmaceutically acceptable gelling agent. In preferred embodiments, the gelling agent forms a gel when dissolved or suspended in an aqueous fluid. In some embodiments of the present invention, the gelling agent is selected from the group consisting of hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatin, and poloxamer. In some preferred embodiments, the gelling agent is hydroxyethyl cellulose.

The present invention contemplates a first protective agent but is not limited to any particular first protective agent. In preferred embodiments, the first protective agent is a pharmaceutically acceptable protective agent. In some embodiments, the first protective agent is selected from the group consisting of non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride. In certain preferred embodiments, the first protective agent is sucrose.

The present invention contemplates compositions comprising a second protective agent but is not limited to any particular second protective agent. In preferred embodiments, the second protective agent is a pharmaceutically acceptable protective agent. In some embodiments comprising a second protective agent, the second protective agent is different from the first protective agent, and is selected from the group consisting of non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride. In some preferred embodiments, the second protective agent is glycerol.

In some embodiments, the present invention provides a composition produced by a method that comprises providing in an aqueous fluid a mixture comprising a probiotic microbe, a pharmaceutically acceptable gelling agent, and a pharmaceutically acceptable first protective agent, freeze-drying the mixture to produce a dried preparation, then exposing the dried preparation to a fluid, e.g., an aqueous fluid, to form a gel comprising an effective amount of the probiotic microbe. In some embodiments, the mixture further comprises a pharmaceutically acceptable second protective agent. In certain embodiments, the probiotic microbe is a strain of E. coli. In some preferred embodiments, the strain of E. coli comprises E. coli 83972 and/or E. coli HU2117.

In some embodiments of the composition of the present invention, the gelling agent is selected from the group consisting of hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatin, and poloxamer. In certain preferred embodiments, the gelling agent is hydroxyethyl cellulose.

In some embodiments, the first protective agent used in the composition formed according to a method of the invention is selected from the group consisting of non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride. In certain preferred embodiments, the first protective agent is sucrose.

In some embodiments comprising a second protective agent, the second protective agent is different from the first protective agent, and is selected from the group consisting of non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, and an amino acid hydrochloride. In some preferred embodiments, the second protective agent is glycerol.

In some embodiments, the effective amount of the probiotic microbe is between about $10^3$ and $10^{11}$ cfu per ml of gel, while in some preferred embodiments, the effective amount of the probiotic microbe is between about $10^5$ and $10^{10}$ cfu per ml of gel. In some particularly preferred embodiments, the effective amount of the probiotic microbe is about $10^7$ and $10^9$ cfu per ml of gel, and in certain particularly preferred embodiments, the effective amount of the microbe is about $10^8$ cfu per ml of gel.

In some embodiments, the gelling agent is present in a concentration of between about 0.1% and 10% w/v in the gel, while in certain embodiments, the gelling agent is present in a concentration of between about 0.5% and 5% w/v in the gel. In some preferred embodiments, the gelling agent is present in a concentration of between about 1% and 3% w/v in the gel, while in particularly preferred embodiments, the gelling agent is present in a concentration of between about 1% and 2% w/v in the gel.

In some embodiments, the first protective agent is present in a concentration of between about 0.1% and 40% w/v in a mixture comprising a probiotic microbe, a gelling agent and a first protective agent, prior to freeze-drying, while in certain embodiments, the first protective agent is present in a concentration of between about 0.2% and 20% w/v in the mixture. In some preferred embodiments, the first protective agent is present in a concentration of between about 0.5% and 15% w/v, while in some particularly preferred embodiments, the first protective agent is present in a concentration of between about 1% and 10% w/v in the mixture In some embodiments comprising a second protective agent, the second protective agent is present in a concentration of between about 0.1% and 40% w/v in a mixture comprising a probiotic microbe, a gelling agent, a first protective agent, and a second protective agent, prior to freeze-drying, while in some embodiments, the second protective agent is present in a concentration of between about 0.2% and 20% w/v in the mixture. In certain preferred embodiments, the second protective agent is present in a concentration of between about 0.5% and 15% w/v in the mixture, and in certain particularly preferred embodiments, the second protective agent is present in a concentration of between about 1% and 10% w/v in the mixture.

In certain embodiments, the probiotic microbe is E. coli HU2117 or E. coli 83972, the gelling agent is hydroxyethyl cellulose, the first protective agent is sucrose and wherein the second protective agent is glycerol. In some embodiments, the probiotic microbe is present in a concentration of about $10^7$ to $10^9$ cfu per ml of gel, and in some embodiments, the hydroxyethyl cellulose is at a concentration of about 2% in the gel. In some preferred embodiments, the sucrose is at a concentration of about 8.3% w/v in the mixture before lyophilization, and in some embodiments, the glycerol is at a concentration of about 1.3% in the mixture before lyophilization.

In some embodiments, the present invention provides a method of administering a probiotic microbe to a subject, comprising providing a freeze-dried preparation comprising a probiotic microbe, a pharmaceutically acceptable gelling agent, and a pharmaceutically acceptable protective agent, exposing the freeze-dried preparation to an aqueous fluid to form a gel comprising an effective amount of the probiotic microbe, and contacting the subject with the gel. In some embodiments, the contacting of the subject with the gel comprises contacting a medical device with the gel to produce a treated device, and contacting the subject with the treated device.

The invention is not limited to any particular method of contacting the device with the gel. For example, in some embodiments, the medical device comprises a surface, and the treated device is at least partially coated with the gel.

While the invention is not limited to use with any particular medical device, in some preferred embodiments, the medical device comprises a urinary catheter. In some embodiments, the urinary catheter comprises an antimicrobial coating, and an effective amount of the probiotic microbe in the gel remains viable in the presence of the antimicrobial coating.

While not limiting the present invention to any particular formulation, in some embodiments, the probiotic microbe comprises *E. coli* HU2117 and/or *E. coli* 83972, the gelling agent comprises hydroxyethyl cellulose, the first protective agent comprises sucrose and the second protective agent comprises glycerol. In certain preferred embodiments, the probiotic microbe in the gel is *E. coli* HU2117 or *E. coli* 83972, the gelling agent in the gel is hydroxyethyl cellulose, the first protective agent in the gel is sucrose and the second protective agent in the gel is glycerol. In some preferred embodiments, the probiotic microbe is present in the gel in a concentration of about $10^7$ to cfu $10^9$ per ml of gel, and in some embodiments, the hydroxyethyl cellulose is at a concentration of about 2% w/v in the gel. In some preferred embodiments, the sucrose is at a concentration of about 8.3% w/v in a mixture comprising a probiotic microbe, a gelling agent, and a first protective agent, prior to lyophilization, and in some embodiments, the glycerol is at a concentration of about 1.3% prior to lyophilization.

In some embodiments, the present invention provides a kit, e.g., for treating a subject, that comprises a composition comprising a probiotic microbe, a pharmaceutically acceptable gelling agent, and a pharmaceutically acceptable first protective agent, in freeze-dried form. In some embodiments of the kit, the composition further comprises a pharmaceutically acceptable second protective agent.

In some embodiments, the kit further comprises a container of sterile aqueous fluid. While not limiting the invention to any particular aqueous fluid, in some preferred embodiments, the sterile aqueous fluid is selected from the group consisting of water and a buffer solution. In some preferred embodiments, the kit of the present invention further comprises a catheter.

While not limiting the kit of the present invention to any particular microbe, in some embodiments, the probiotic microbe is a strain of *E. coli*. In certain preferred embodiments, the strain of *E. coli* comprises *E. coli* 83972 and/or *E. coli* HU2117.

Embodiments of the invention are described in this summary, and in the Detailed Description of the Invention, below, which is incorporated here by reference. Although the invention has been described in connection with specific embodiments, it should be understood that the invention as claimed should not be unduly limited to such specific embodiments.

DEFINITIONS

To facilitate an understanding of the present invention, a number of terms and phrases are defined below:

As used herein, the term "subject" refers to individuals (e.g., human, animal, or other organism) to be treated by the methods or compositions of the present invention. Subjects include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a probiotic microbe, and optionally one or more other agents) for a condition characterized by the presence of pathogenic bacteria, or in anticipation of possible exposure to pathogenic bacteria.

The term "diagnosed," as used herein, refers to the recognition of a disease (e.g., caused by the presence of pathogenic bacteria) by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "virulence" refers to the degree of pathogenicity of a microorganism, e.g., as indicated by the severity of the disease produced or its ability to invade the tissues of a subject. It is generally measured experimentally by the median lethal dose ($LD_{50}$) or median infective dose ($ID_{50}$). The term may also be used to refer to the competence of any infectious agent to produce pathologic effects.

As used herein, the term "effective amount" refers to the amount of a composition (e.g., a probiotic microbe) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "treating a surface" refers to the act of exposing a surface to one or more compositions of the present invention. Methods of treating a surface include, but are not limited to, spraying, misting, submerging, and coating.

As used herein, the term "co-administration" refers to the administration of at least two agent(s) (e.g., two separate donor bacteria, each comprising a different plasmid) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., a probiotic microbe) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present invention may be formulated for horticultural or agricultural use. Such formulations include dips, sprays, seed dressings, stem injections, sprays, and mists.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "medical devices" includes any material or device that is used on, in, or through a subject's or patient's body, for example, in the course of medical treatment (e.g., for a disease or injury). Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, intrauterine devices (IUDs), diaphragms, and condoms.

As used herein, the term "therapeutic agent," refers to compositions that decrease the infectivity, morbidity, or onset of mortality in a subject contacted by a pathogenic microorganism or that prevent infectivity, morbidity, or onset of mortality in a host contacted by a pathogenic microorganism. As used herein, therapeutic agents encompass agents used prophylactically, e.g., in the absence of a pathogen, in view of possible future exposure to a pathogen. Such agents may additionally comprise pharmaceutically acceptable compounds (e.g., adjuvants, excipients, stabilizers, diluents, and the like). In some embodiments, the therapeutic agents of the present invention are administered in the form of topical compositions, injectable compositions, ingestible compositions, and the like. When the route is topical, the form may be, for example, a solution, cream, ointment, salve or spray.

As used herein, the term "pathogen" refers to a biological agent that causes a disease state (e.g., infection, cancer, etc.)

in a host. "Pathogens" include, but are not limited to, viruses, bacteria, archaea, fungi, protozoans, mycoplasma, prions, and parasitic organisms.

As used herein, the terms "probiotic" and "probiotic microbe" are used interchangeably to refer to a live microorganism that is administered in adequate amounts to confer a health benefit on the host. See, e.g., *Potential Uses of Probiotics in Clinical Practice*, G. Reid, et al., Clinical Microbiology Reviews, October 2003, p 658-672, incorporated herein by reference. Probiotics are not limited to microorganisms administered by any particular route. Exemplary routes of administration to the human body can be through the eyes (ophthalmic), mouth (oral), skin (transdermal), nose (nasal), lungs (inhalant), oral mucosa (buccal), vagina, rectum, urethra, ear, by injection (e.g., intravenously, subcutaneously, intratumorally, intraperitoneally, etc.) and the like. As used herein, the term "probiotic" includes but is not limited to naturally occurring organisms and derivatives thereof, e.g., *E. coli* 83972, and *E. coli* HU2117. Probiotic organisms may also be modified, e.g., through selective culturing or recombinant engineering, to have altered properties. For example, probiotic microbes configured to contain conjugatively transmissible plasmids that alter recipient cells (e.g., to kill or to reduce pathogenicity of a pathogen recipient cell) also find use with the present invention. See, e.g., U.S. application Ser. Nos. 11/137,950 and 11/137,948, each of which is incorporated herein by reference in its entirety.

As used herein, the term "microbe" refers to a microorganism and is intended to encompass both an individual organism, or a preparation comprising any number of the organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram stain, causing the stained cells to generally appear dark blue to purple under the microscope. "Gram-negative bacteria" do not retain the primary dye used in the Gram stain, but are stained by the counterstain. Thus, Gram-negative bacteria generally appear red.

As used herein, the term "microorganism" refers to any species or type of microorganism, including but not limited to, bacteria, archaea, fungi, protozoans, mycoplasma, and parasitic organisms. The present invention contemplates that a number of microorganisms encompassed therein will also be pathogenic to a subject.

As used herein, the term "fungi" is used in reference to eukaryotic organisms such as the molds and yeasts, including dimorphic fungi.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram-stain, causing the stained cells to generally appear dark blue to purple under the microscope. "Gram-negative bacteria" do not retain the primary dye used in the Gram-stain, but are stained by the counterstain. Thus, Gram-negative bacteria generally appear red.

The term "non-pathogenic bacteria" or "non-pathogenic bacterium" includes all known and unknown non-pathogenic bacterium (Gram-positive or Gram-negative) and any pathogenic bacterium that has been mutated or converted to a non-pathogenic bacterium. Furthermore, a skilled artisan recognizes that some bacteria may be pathogenic to specific species and non-pathogenic to other species; thus, these bacteria can be utilized in the species in which it is non-pathogenic or mutated so that it is non-pathogenic.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells, including, e.g., prokaryotic cells and eukaryotic cells. Included within this term are continuous cell lines (e.g., with an immortal phenotype), primary cell cultures, transformed cell lines, finite cell lines (e.g., non-transformed cells), bacterial cultures in or on solid or liquid media, and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "kit" refers to any delivery system for delivering materials. In the context of reaction materials such as probiotic microbes, such delivery systems include but are not limited to systems that allow for the storage, transport, or delivery of appropriate reagents (e.g., cells, buffers, culture media, selection reagents, etc., in the appropriate containers) and/or devices (e.g., catheters, syringes, reaction tubes or plates, culture tubes or plates) and/or supporting materials (e.g., media, written instructions for performing using the materials, etc.) from one location to another. For example, kits include one or more enclosures (e.g., boxes, bags) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain a dried composition of a microbe with a gelling agent for a particular use, while a second container contains sterile fluid such as water or buffer for dissolving or resuspending a dried composition. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction materials needed for a particular use in a single container (e.g., in a single box housing each of the desired components). The term "kit" includes both fragmented and combined kits.

With regards to the dried cake produced by lyophilization of a composition, the term "elegant" is used in the literature to describe a 'perfect' lyophilization product with no cracks, no shrinkage, with smooth edges, and a fluffy consistency.

As used herein, the terms "a" and "an" means at least one, and may refer to more than one.

The term "bacterial interference" as used herein is refers to an antagonistic interaction among bacteria to establish themselves and dominate their environment. Bacterial interference operates through several mechanisms, i.e., production of antagonistic substances, changes in the bacterial microenvironment, and reduction of needed nutritional substances.

The term "coating" as used herein refers to a layer of material covering, e.g., a medical device or a portion thereof. A coating can be applied to the surface or impregnated within the material of the implant.

The term "effective amount" means a sufficient amount of an agent, e.g., a probiotic or an antimicrobial agent, to produce a beneficial effect to the host, e.g., by decreasing, preventing, or inhibiting the growth of bacterial and/or fungal organisms. It is within the skilled artisan's ability to relatively easily determine an effective amount of a probiotic microbe or other therapeutic composition.

As used herein, the term "antimicrobial agent" refers to composition other than a probiotic that decreases, prevents or inhibits the growth of bacterial and/or fungal organisms. Examples of antimicrobial agents include, e.g., antibiotics and antiseptics.

The term "antiseptic" as used herein is defined as an antimicrobial substance that inhibits the action of microorganisms, including but not limited to alpha.-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, silver, benzyl peroxide, alcohols, and carboxylic acids and salts. One skilled in the art is cognizant that these antiseptics can be used in combinations of two or more to obtain a synergistic effect. Some examples of combinations of antiseptics include a mixture of chlorhexidine, chlorhexidine and chloroxylenol, chlorhexidine and methylisothiazolone, chlorhexidine and (.alpha.-terpineol, methylisothiazolone and alpha.-terpineol; thymol and chloroxylenol; chlorhexidine and cetylpyridinium chloride; or chlorhexidine, methylisothiazolone and thymol. These combinations provide a broad spectrum of activity against a wide variety of organisms.

The term "antibiotics" as used herein is defined as a substance that inhibits the growth of microorganisms without damage to the host. For example, the antibiotic may inhibit cell wall synthesis, protein synthesis, nucleic acid synthesis, or alter cell membrane function.

Classes of antibiotics include, but are not limited to, macrolides (e.g., erythromycin), penicillins (e.g., nafcillin), cephalosporins (e.g., cefazolin), carbepenems (e.g., imipenem), monobactam (e.g., aztreonam), other beta-lactam antibiotics, beta-lactam inhibitors (e.g., sulbactam), oxalines (e.g. linezolid), aminoglycosides (e.g., gentamicin), chloramphenicol, sulfonamides (e.g., sulfamethoxazole), glycopeptides (e.g., vancomycin), quinolones (e.g., ciprofloxacin), tetracyclines (e.g., minocycline), fusidic acid, trimethoprim, metronidazole, clindamycin, mupirocin, rifamycins (e.g., rifampin), streptogramins (e.g., quinupristin and dalfopristin) lipoprotein (e.g., daptomycin), polyenes (e.g., amphotericin B), azoles (e.g., fluconazole), and echinocandins (e.g., caspofungin acetate).

Examples of specific antibiotics include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al, U.S. Pat. No. 4,642,104 herein incorporated by reference will readily suggest themselves to those of ordinary skill in the art.

As used here, the term "resistant" as applied to a microbe in reference to an antimicrobial agent refers to a microbe that retains sufficient viability in the presence of an antimicrobial agent that the resistant microbe can be used as a probiotic in the presence of the antimicrobial agent. One of skill in the art will appreciate that both the viability of the microbe and the concentration of the antimicrobial agent are variable, such that, e.g., a moderately resistant microbe may find use in applications where a concentration of an antimicrobial agent is low (e.g., residual antimicrobial agent from a prior treatment) and a highly resistant microbe may find use in applications where a concentration of an antimicrobial agent is high (e.g., co-administration of a probiotic and an antimicrobial agent).

As used herein, the term "dried" as used in reference to a probiotic composition refers to removing the solvent component or components to levels that no longer support chemical reactions. The term is also used in reference to a composition that has been dried (e.g., a dried preparation or dried composition). Those of skill in the art will appreciate that a composition may be "dried" while still having residual solvent or moisture content after lyophilization, or that a dried composition may, after the end of the drying process, absorb moisture hygroscopically, e.g., from the atmosphere. The term "dried" encompasses a composition with increased moisture content due to hygroscopic absorption.

As used herein, the term "protective agent" refers to a composition or compound that protects the activity or integrity of an active agent (e.g., an enzyme, a probiotic microbe) when the active agent is exposed to certain conditions (e.g., drying, freezing). In some embodiments, a protective agent protects a living organism (e.g., a probiotic microbe) during a freezing process (i.e., it is a "cryoprotectant"). Examples of protective agents include but are not limited to non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride.

As used herein, the term "gelling agent" refers to a composition that, when dissolved, suspended or dispersed in a fluid (e.g., an aqueous fluid such as water or a buffer solution), forms a gelatinous semi-solid (e.g., a lubricant gel). Examples of gelling agents include but are not limited to hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatin, and poloxamer.

As used herein, the term "excipient" refers to an inactive ingredient (i.e., not pharmaceutically active) added to a preparation of an active ingredient. The gelling and protective agents described herein are referred to generally as "excipients."

DETAILED DESCRIPTION OF THE INVENTION

The present invention relates to compositions and methods for delivering effective amounts of viable probiotic microbes to a subject. In some embodiments, the invention relates to compositions for storage and/or administration of effective amounts of probiotic microbes. In some embodiments, the invention relates to methods of preparing compositions of microbes, e.g., for convenient storage and/or administration, of effective therapeutic amounts of the probiotic microbes. In some embodiments, the invention relates to methods of treatment comprising preparation and/or administration of probiotic microbes.

While not limiting the present invention to any particular configuration, it is observed that, in preferred embodiments, the methods and compositions of the present invention provide a therapeutic delivery system or formulation that is non-toxic, e.g., to humans. In some particularly preferred embodiments, the formulations of the present invention make use of substances approved by the FDA for use in the urinary tract and/or bladder. In particularly preferred embodiments, the compositions of the present invention can be adopted for use in medical procedures, e.g., catheterization, with minimal or no change to common catheterization methods and procedures.

For clarity, the Detailed Description of the Invention is provided in the following sections: I. Bacterial Interference; II. Compositions of probiotic microbes; III. Methods of administering probiotic compositions; IV. Kits for providing probiotic compositions.

I. Bacterial Interference

The principle of bacterial interference in the prevention of CAUTI has been investigated. Bacterial interference refers to the principle of using probiotics to prevent colonization with other types of bacteria, e.g., pathogens. Administered probiotic bacteria can interfere with the growth of a pathogenic strain by virtue e.g., of bacterial excretions, or competition for nutrients, although use of bacterial interference is not limited to any particular mechanism. This approach has excellent theoretical underpinnings and may offer a good solution for symptomatic UTI in the neurogenic bladder (Srinivasan, A., T. Karchmer, et al., *Infect Control Hosp Epidemiol* 27(1): 38-43 (2006)).

Bacterial interference can be either passive or active (Reid, Howard et al. 2001). In the case of UTI and neurogenic bladder, passive bacterial interference occurs when asymptomatic colonization is left untreated in order to prevent subsequent colonization with virulent organisms. Active interference involves the introduction into the bladder of a specific bacterial strain or strains with beneficial characteristics, with the intent of preventing infection with virulent strains.

All clinical studies on active interference for the prevention of CAUTI thus far have used the approach of directly inoculating a non-pathogenic strain of *E. coli* (e.g., *E. coli* 83972) into the bladder. However, this approach is cumbersome and can require multiple attempts to induce colonization. An alternative approach that appears to have promise is the incubation of the catheter itself with *E. coli* 83972, to create a biofilm on the catheter. An in vitro study showed that pre-exposure of the catheter to *E. coli* 83972 significantly reduced the number of uropathogens colonizing the catheter surface after insertion, compared to vehicle control treated catheters (Roos, V., G. C. Ulett, et al., *Infect Immun* 74(1): 615-24 (2006)). Preliminary data from a pilot study of pre-treated catheters inserted in 12 subjects with neurogenic bladder showed that the colonization rate after 30 days was 92%, suggesting that this method of colonization may be very efficient (R. Darouiche, personal communication). However, incubation of catheters to provide a biofilm prior to use of the catheter is burdensome in that it can require additional facilities, and requires a significant alteration in the ordinary procedure for urinary catheterization.

The present invention provides improved compositions and methods for administering probiotic microbes. While not limited to any particular application, the methods and compositions find use in the treatment and prevention of catheter associated urinary tract infections. The present invention provides formulations of probiotics for use, e.g., with a conventional urinary catheter, with minimal alteration of standard protocols for catheterization. In some embodiments, the probiotic microbe compositions of the present invention may be used in conjunction with, or following treatment of a device or subject with an antimicrobial agent, such as an antiseptic or an antibiotic. In some preferred embodiments, the probiotic microbe employed is resistant to the antimicrobial agent with which it is used.

II. Compositions of Probiotic Microbes

In some embodiments, the present invention provides compositions of probiotic microbes that are formulated for application to a catheter prior to insertion. In particular, in certain embodiments, the present invention provides compositions comprising probiotics that are configured to be used, e.g., by a clinician, without the need to culture the probiotic organism prior to administration.

In some embodiments, the probiotic microbe is a bacterium and, in certain embodiments, the bacterium is selected from the group consisting of Enterobacteriacae, *Pseudomonas aeruginosa*, *Stenotrophomonas maltophilia*, *Burkholderia cepacia*, *Gardnerella vaginalis*, and *Acinetobacter* species. In some specific embodiments, the probiotic organism is *Pseudomonas aeruginosa*.

In some preferred embodiments, a probiotic bacterium is selected from the group of Enterobacteriacea consisting of *Escherichia*, *Shigella*, *Edwardsiella*, *Salmonella*, *Citrobacter*, *Klebsiella*, *Enterobacter*, *Hafnia*, *Serratia*, *Proteus*, *Morganella*, *Providencia*, *Yersinia*, *Erwinia*, *Buttlauxella*, *Cedecea*, *Ewingella*, *Kluyvera*, *Tatumella* and *Rahnella*.

In some particularly preferred embodiments, the bacterium is Enterobacteriacea and is selected from the group of *Escherichia coli* 83972 or mutants thereof. *Escherichia coli* 83972 is a clinical isolate associated with asymptomatic bacteriuria (Andersson' et al., 1991, Infect. Immun. 59:2915-2921) and the strain has been used to successfully colonize bladders of human volunteers. *E. coli* HU2117 is a variant of 83972 having a deleted papG83972 gene, and it has also been shown to successfully colonize the bladders of human subjects (Hull, et al., 2002, Infection and Immunity, 70 (11): 6481-6481).

In some preferred embodiments of the present invention, the probiotic bacterium is a bacterium that adheres to urinary catheters. In some embodiments, the bacterium having adherent properties is selected from the group consisting of *Providencia*, *Proteus*, *Pseudomonas aeruginosa* and *Escherichia coli*.

Those of skill in the art will appreciate that the compositions of the present invention are not limited to those containing a single species or type of microbe. It is contemplated that combinations of probiotic organisms may be used in the methods and compositions disclosed herein.

In some embodiments, the present invention provides a preparation of a probiotic microbe configured for stable storage, e.g., a freeze-dried preparation. While an understanding of the mechanism is not required to practice the present invention, and while not limiting the invention to any particular mechanism, freeze-drying, or "lyophilization" generally stabilizes a formulation by removing the solvent component or components to levels that no longer support chemical reactions. This removal is accomplished by first freezing the formulation, thus separating the solutes from the solvent. The solvent is then removed by drying, or sublimation, while the sample remains frozen. In some embodiments, the procedure comprises removal of solvent(s) by primary drying, followed by a secondary drying or desorption.

Formulations for freeze-drying generally comprise at least the active ingredient, e.g., a probiotic microbe, and a solvent system (e.g., water, in the case of an aqueous liquid). Formulations of the present invention generally further comprise a protective agent.

In the freezing of formulations containing biological organisms, the formation of ice within a cell leads to cell membrane rupture, thus destroying the organism. In preferred embodiments, a protective protects the probiotic microbe during the freezing process (i.e., it is a "cryoprotectant"). The present invention is not limited to any particular cryoprotectant. Cryoprotectants finding use in the methods and compositions of the present invention include, e.g., non-fat milk solids, trehalose, glycerol, betaine, sucrose, glucose, lactose, polymers such as dextran and polyethylene glycol, sorbitol, mannitol, poly vinyl propylene (PVP), potassium glutamate, monosodium glutamate, Tween 20 detergent, Tween 80 detergent, Nonidet-P40, and amino acids, such as proline, histidine, arginine hydrochloride, glycine, lysine, glutanuc acid, aspartic acid, etc. In some preferred embodiments, the protective agent is included in the formulation prior to freezing in a concentration of about 0.1% to 20% w/v.

Those of skill in the art will appreciate that the compositions of the present invention are not limited to those containing a single protective agent. It is contemplated that combinations of protective agents may be used in the methods and compositions of the present invention.

In some embodiments, the protective agent also serves as a bulking agent. Some formulations may result in cake that has poor structural qualities, or that leaves the container during the drying process. The addition of bulking agents such as mannitol and dextran may strengthen cake structure. It is contemplated that, in some embodiments, formulations of the present invention may additionally contain excipients or bulking agents that are not protective agents.

In preferred embodiments, the composition comprises an agent to facilitate administration of a reconstituted (e.g., resuspended) composition. For example, in preferred embodiments comprising a freeze-dried preparation, the composition further comprises a gelling agent, such that the resuspension of the dried preparation results in a gel. Gels have numerous beneficial properties for administration of a composition, e.g., to a device or a subject, including but not limited to lubricant properties, and the properties of resisting running or dripping after application. The invention is not limited to any particular gelling agent. Gelling agents finding use in the methods and compositions of the present invention include, e.g., hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatins (e.g., recombinant and/or hydrolyzed animal gelatins), and poloxamer (e.g., Lutrol F127). In some preferred embodiments, the gelling agent is included in the gel composition in a concentration of about 0.1% to 20% w/v.

Those of skill in the art will appreciate that the compositions of the present invention are not limited to those containing a single gelling agent. It is contemplated that combinations of gelling agents may be used in the methods and compositions disclosed herein.

In some preferred embodiments, the present invention provides a composition comprising a probiotic microbe, a pharmaceutically acceptable gelling agent, and a pharmaceutically acceptable first protective agent, in freeze-dried form. In some embodiments, the composition further comprises a pharmaceutically acceptable second protective agent. In some preferred embodiments, the second protective agent is included in the formulation prior to freezing in a concentration of about 0.1% to 20% w/v.

In some embodiments, the present invention provides methods of making the compositions described above. In some embodiments, the methods comprise providing a fluid mixture comprising a probiotic microbe, a protective agent, and a gelling agent, and freeze-drying the mixture to produce a dried preparation.

In some embodiments, the solvent system is a completely aqueous solution, while in other embodiments, the solvent system contains other solvents, such as an alcohol. In some embodiments, the solvent system comprises a buffer that provides dried buffer components to the freeze-dried composition.

In certain embodiments, the solvent is first removed by sublimation while the temperature of the frozen matrix is maintained below the eutectic (eutectic temperature is a point on a phase diagram where the temperature of the system or the concentration of the solution at the point cannot be altered without changing the number of phases present) or collapse temperature of the formulation. This is the primary drying process. The chamber pressure and product and shelf temperatures during primary drying are generally based on the formulation's eutectic or collapse temperature.

In preferred embodiments, after primary drying, residual moisture on the resulting cake surface is reduced to levels that no longer support biological growth and chemical reactions. This process is referred to as secondary drying. The reduction of moisture in the cake during secondary drying is generally accomplished by increasing the shelf temperature and reducing the partial pressure of water vapor in the container. The required partial pressure of water vapor and shelf temperature are generally ascertained from stability studies of lyophilized or vacuum-dried products having varied amounts of residual moisture.

In some embodiments, lyophilization is conducted essentially according to the procedure described in Table 1, below. In some preferred embodiments, lyophilization is conducted essentially according to the procedure described in Table 2, below, while in particularly preferred embodiments, lyophilization is conducted essentially according to the procedure described in Table 3, below.

In some embodiments, the methods of the present invention further comprise a step of dissolving or resuspending the dried probiotic composition in a fluid, e.g., sterile water. In preferred embodiments, the dried composition comprises a gelling agent, and resuspension of the cake in fluid produces a gel.

III. Methods of Administering Probiotic Compositions

In some embodiments, the present invention provides a method of administering a probiotic microbe to a subject, comprising providing a freeze-dried preparation comprising a probiotic microbe, a gelling agent, and a protective agent, exposing said freeze-dried preparation to an aqueous fluid to form a gel comprising an effective amount of said probiotic microbe, and contacting said subject with said gel. In some preferred embodiments, the step of contacting the subject with the gel comprises contacting a device, e.g., a medical device with the gel, then contacting the medical device with the subject. In preferred embodiments, the device is a urinary catheter.

A specific embodiment of the present invention is a method for coating a medical device comprising the steps of applying to at least a portion of the surface of the device a gel composition comprising a probiotic microbe present in an effective amount to inhibit the growth of bacterial and fungal organisms relative to an uncoated medical device.

In some preferred embodiments, the gel comprising the probiotic microbe is used in conjunction with a conventional catheter lubricant (e.g., SteriLub lubricant, SurgiLube, lubricant, KY Jelly) prior to catheter insertion. In particularly preferred embodiments, the gel comprising the probiotic microbe is used in place of a conventional catheter lubricant prior to catheter insertion.

IV. Kits for Providing Probiotic Compositions

One aspect of the present invention is to provide kits or trays comprising one or more components for e.g., for treating a subject. In preferred embodiments, a kit is configured for easy delivery to and use by medical personnel, e.g., in a hospital, clinic, or medical office. In some embodiments, a kit according to the present invention is configured to be used in conjunction with a standard catherization kit or tray, while in other embodiments, a kit according to the present invention is configured to replace a standard catheterization kit or tray. In preferred embodiments, the kit comprises all necessary components for catheterization according to the methods of the present invention.

In some embodiments, the kit provides, e.g., in a container, a freeze-dried composition comprising a probiotic microbe, a pharmaceutically acceptable gelling agent, and a pharmaceutically acceptable first protective agent. In some embodiments of the kit, the composition further comprises a pharmaceutically acceptable second protective agent.

In some embodiments, the kit further comprises a container of sterile fluid, e.g., an aqueous fluid such as water or a buffer solution, for suspending dried composition to form a lubricant gel, e.g., for use in inserting a catheter. In some preferred embodiments, the kit of the present invention further comprises a catheter.

While not limiting the kit of the present invention to any particular microbe, in some embodiments, the probiotic microbe is a strain of E. coli. In certain preferred embodiments, the strain of E. coli comprises E. coli 83972 and/or E. coli HU2117.

A kit according to the present invention is not limited to components related to catheterization, and may comprise additional components, e.g., components related to patient care, including but not limited to trays, underpads, swabs, antiseptic wipes, tissues, tape, gloves, drapes, specimen containers, syringes, etc.

EXPERIMENTAL

The following examples are provided in order to demonstrate and further illustrate certain preferred embodiments and aspects of the present invention and are not to be construed as limiting the scope thereof.

In the experimental disclosure that follows, the following abbreviations apply: ° C. (degrees Celsius); cm (centimeters); g (grams); 1 or L (liters); ml or mL (milliliters); µl or µL (microliters); µg (micrograms); µl (microliters); µm (micrometers); µM (micromolar); µmol (micromoles); mg (milligrams); ml (milliliters); mm (millimeters); mM (millimolar); mmol (millimoles); M (molar); mol (moles); ng (nanograms); nm (nanometers); nmol (nanomoles); N (normal); pmol (picomoles); bp (base pairs); cfu (colony forming units).

By way of example and not by way of limitation, the following experiments describe the effects of different excipients and lyophilization protocols on the viability of E. coli strain HU2117. Starting quantities were selected so as to maintain an effective level of viability in cells freeze-dried in a composition comprising a gelling agent. For example, in some embodiments, a preferred concentration of viable cells might be approximately $10^8$ cfu/ml. If a vial (or other container) of the preparation of the present invention is to be suspended or dissolved, e.g., in 10 ml of water, the dried cake in the vial would optimally have approximately $10^9$ viable cells. Once a protocol is assessed for the percentage of cells that remain viable after processing, one can easily calculate an approximate number of cells to start with to obtain a cake having any particular desired number of viable cells.

Example 1

Preparation of Freeze-Dried E. coli HU2117

Protocol 1

The goal of the investigation was to examine the effects of different excipients and conditions for lyophilization of HU2117, so as to maintain an effective cell concentration and level of viability of cells freeze-dried in a composition comprising a gelling agent.

Cell Preparation

Two flasks of cells (Flask A and Flask B) were grown, each from 1 ml of seed stock inoculated into 1 L modified EZ Rich Defined Glycerol medium, incubated at 37±1° C. for 8 hrs with constant shaking at 250 RPM. At the end of 8 hours, the $OD_{600}$ of Flask A was 2.53 and the $OD_{600}$ of Flask B was 1.11.

The cells were collected by centrifugation at 4° C., at 6000 RPM for 8 min. The pelleted cells were washed twice with 0.9% saline and once with 10 mM citrate buffer, pH 7.0. The cells pelleted from each liter of culture were resuspended into 2-3 ml of 10 mM citrate buffer, pH 7.0, for a final volume of approximately 5 ml.

The concentration of resuspended cells was determined using plate counts. The Flask A preparation had a viable cell concentration of $2.8 \pm 1.2 \times 10^{11}$ CFU/ml, and the Flask B preparation had a viable cell concentration of $1.8 \pm 0.2 \times 10^{11}$ CFU/ml. The cells from Flask A and Flask B were pooled and used for lyophilization tests.

Lyophilization

For each test, 0.5 ml of resuspended cells were mixed with 1.5 ml of an excipient selected from the list below and 10 ml of 2% autoclaved hydroxyethyl cellulose (HEC).

Excipients (shown as the concentration (w/v) that would be achieved if the dried cake is resuspended to a final volume of 10 ml; if a different volume of fluid is used for dissolving the cake, the concentrations vary proportionally):
(a) buffer (no excipients)
(b) 2% HEC
(c) 2% HEC+1.5% Glycerol
(d) 2% HEC+5% Trehalose
(e) 2% HEC+5% Sucrose
(f) 2% HEC+10% Trehalose
(g) 2% HEC+10% Sucrose
(h) 2% HEC+5% Trehalose+1.5% Glycerol
(i) 2% HEC+5% Sucrose+1.5% Glycerol
(j) 2% HEC+10% Trehalose+1.5% Glycerol
(k) 2% HEC+10% sucrose+1.5% Glycerol The cell-excipient mixtures were lyophilized as described in Table 1 to produce dried cakes.

TABLE 1

| Process step | Step description |
|---|---|
| Loading | Incubate at 5° C. and one atmosphere for 60 min. |
| Freezing | Ramp shelf to −45° C. at an average controlled rate of 5° C./min. Control shelf at target set point of −45° C. for 300 min. |
| Primary drying | Evacuate chamber, control at a target set point of 100 mTorr. Ramp shelf to −35° C. at an average controlled rate of 0.5° C./min. Control shelf at target set point of −35° C. for 2850 min. |
| Secondary drying | Control chamber pressure at a target set point of 100 mTorr. Ramp shelf to 25° C. at controlled average rate of 0.2° C./min. Control shelf at target set point for 720 min |

Sublimation was not complete at the end of primary drying and a new cycle was started, with primary drying temperature at −28° C. at an average controlled rate of 0.5° C./min for 18 hrs, and secondary drying temperature set to 20° C. for 720 min. After drying, each cake was resuspended in 12 ml of $H_2O$ Following the protocol above produced the following observations:
(a) The lyophilization cake was shrunk and showed phase separation except in the presence of excipients (f), (g), (j) and (k), listed above.
(b) Solubility during reconstitution of the cake was good in presence of excipient (c), (g), (j) and (k), listed above.
(c) Cake in the absence of excipients (i.e., buffer alone used in place of excipients) or using conditions of 10% Trehalose or (5% Sucrose+1.5% Glycerol) had undissolved particles after reconstituting the cake with water.

The viability of the resuspended cells was tested, with the results shown in Table 2

TABLE 2

(% Viability)

| | Protective agents | | | |
|---|---|---|---|---|
| Concentration w/v Before Lyophilization | Concentration w/v after Resuspension of Cake in 12 ml $H_2O$ | Viability Before Lyophilization (cfu) | Viability After Lyophilization (cfu) | Viability Percentage |
| Resuspended Pellet | Not applicable | $32 \times 10^{10}$ | N/A | N/A |
| | | $16 \times 10^{10}$ | N/A | N/A |
| | | $36 \times 10^{10}$ | N/A | N/A |
| Average | | $2.8 \pm 1.2 \times 10^{11}$ | N/A | N/A |
| 1.7% HEC | 1.7% HEC | $52 \times 10^8$ | $14 \times 10^6$ | 0.27 |
| | | $86 \times 10^8$ | $20 \times 10^6$ | 0.25 |
| | | $102 \times 10^8$ | $30 \times 10^6$ | 0.29 |
| | Average | $8.0 \pm 3.8 \times 10^9$ | $(2.1 \pm 0.7) \times 10^6$ | $0.27 \pm 0.02\%$ |
| 1.7% HEC + 1.3% Glycerol | 1.7% HEC + 1.3% Glycerol | N/A | $20 \times 10^5$ | 0.02 |
| | | N/A | $58 \times 10^5$ | 0.06 |
| | | N/A | $22 \times 10^5$ | 0.02 |
| | Average | $9.5 \pm 2.1 \times 10^9$ | $(3.3 \pm 1.3) \times 10^6$ | $0.034 \pm 0.03\%$ |
| 1.7% HEC + 4.2% Trehalose | 1.7% HEC + 4.2% Trehalose | N/A | $28 \times 10^6$ | 0.29 |
| | | N/A | $12 \times 10^6$ | 0.13 |
| | | N/A | $22 \times 10^6$ | 0.23 |
| | Average | $9.5 \pm 2.1 \times 10^9$ | $(2.1 \pm 0.7) \times 10^7$ | $0.22 \pm 0.09\%$ |
| 1.7% HEC + 4.2% Sucrose | 1.7% HEC + 4.2% Sucrose | N/A | $52 \times 10^7$ | 5.5 |
| | | N/A | $32 \times 10^7$ | 3.4 |
| | | N/A | $20 \times 10^7$ | 2.1 |
| | Average | $9.5 \pm 2.1 \times 10^9$ | $(3.5 \pm 1.7) \times 10^8$ | $3.7 \pm 1.8\%$ |
| 1.7% HEC + 8.3% Trehalose | 1.7% HEC + 8.3% Trehalose | N/A | $10 \times 10^6$ | 0.1 |
| | | N/A | $12 \times 10^6$ | 0.1 |
| | | N/A | $18 \times 10^6$ | 0.2 |
| | Average | $9.5 \pm 2.1 \times 10^9$ | $(1.3 \pm 0.5) \times 10^7$ | $0.13 \pm 0.07\%$ |
| 1.7% HEC + 8.3% Sucrose | 1.7% HEC + 8.3% Sucrose | N/A | $34 \times 10^8$ | 35.8 |
| | | N/A | $14 \times 10^8$ | 14.7 |
| | | N/A | $14 \times 10^8$ | 14.7 |
| | Average | $9.5 \pm 2.1 \times 10^9$ | $(2.1 \pm 1.3) \times 10^9$ | $21.7 \pm 14.1\%$ |
| 1.7% HEC + 4.2% Trehalose + 1.3% Glycerol | 1.7% HEC + 4.2% Trehalose + 1.3% Glycerol | N/A | $72 \times 10^7$ | 7.6 |
| | | N/A | $48 \times 10^7$ | 5.0 |
| | | N/A | $56 \times 10^7$ | 5.9 |
| | Average | $9.5 \pm 2.1 \times 10^9$ | $(5.9 \pm 1.3) \times 10^8$ | $6.2 \pm 1.4\%$ |
| 1.7% HEC + 4.2% Sucrose + 1.3% Glycerol | 1.7% HEC + 4.2% Sucrose + 1.3% Glycerol | N/A | $40 \times 10^7$ | 4.2 |
| | | N/A | $102 \times 10^7$ | 10.7 |

TABLE 2-continued (% Viability)

| Concentration w/v Before Lyophilization | Concentration w/v after Resuspension of Cake in 12 ml $H_2O$ | Viability Before Lyophilization (cfu) | Viability After Lyophilization (cfu) | Viability Percentage |
|---|---|---|---|---|
| | | N/A | $58 \times 10^7$ | 6.1 |
| | Average | $9.5 \pm 2.1 \times 10^9$ | $(6.7 \pm 0.3) \times 10^9$ | $7.0 \pm 3.7\%$ |
| 1.7% HEC + 8.3% Trehalose + 1.3% Glycerol | 1.7% HEC + 8.3% Trehalose + 1.3% Glycerol | N/A | $58 \times 10^7$ | 6.1 |
| | | N/A | $56 \times 10^7$ | 5.9 |
| | | N/A | $66 \times 10^7$ | 6.9 |
| | Average | $9.5 \pm 2.1 \times 10^9$ | $(6.0 \pm 0.6) \times 10^9$ | $6.3 \pm 0.6\%$ |
| 1.7% HEC + 8.3% Sucrose + 1.3% Glycerol | 1.7% HEC + 8.3% Sucrose + 1.3% Glycerol | $116 \times 10^8$ | $20 \times 10^8$ | 17.24 |
| | | $84 \times 10^8$ | $32 \times 10^8$ | 38.1 |
| | | $86 \times 10^8$ | $14 \times 10^8$ | 16.3 |
| | Average | $9.5 \pm 2.1 \times 10^9$ | $(2.2 \pm 0.8) \times 10^9$ | $23.9 \pm 7.6\%$ |

While not limiting the present invention to any particular minimum of viability, it is observed that, using these experimental conditions, 2% HEC+10% Sucrose, in the presence or absence of 1.5% Glycerol, allows for >20% viability after lyophilization.

Example 2

Preparation of Freeze-Dried *E. coli* HU2117

Protocol 2

Cell Preparation

Two flasks of cells (Flask A and Flask B) were grown, each from 1 ml of seed stock inoculated into 1 L Modified EZ Rich Defined Glycerol medium, incubated at 37±1° C. for 8 hrs with constant shaking at 250 RPM. At the end of 8 hours, the $OD_{600}$ of Flask A was 1.89 and the $OD_{600}$ of Flask B was 1.53.

The cells were collected by centrifugation at 4° C., at 6000 RPM for 8 min. The pelleted cells were washed twice with 0.9% saline and washed once with 10 mM citrate buffer, pH 7.0.

The cells pelleted from each liter of culture were resuspended into 2-3 ml of 10 mM citrate buffer, pH 7.0, for a final volume approximately 5 ml.

The concentration of the resuspended cells was determined using plate counts. Resuspended cells from Flask A had a viable cell concentration of $1.2 \pm 0.3 \times 10^{11}$ CFU/ml, and resuspended cells from Flask B had a viable cell concentration of $7.7 \pm 0.3 \times 10^{10}$ CFU/ml. The cells from Flask A and Flask B were pooled and used for lyophilization tests.

Lyophilization

For each test, 0.5 ml of resuspended cells were mixed with 1.5 ml of an excipient selected from the list below and 10 ml of 1% autoclaved hydroxyethyl cellulose (HEC).

Excipients (shown as the concentration (w/v) that would be achieved if the dried cake is resuspended to a final volume of 10 ml; if a different volume of fluid is used for dissolving the cake, the concentrations vary proportionally):
  (a) buffer
  (b) 1% HEC
  (c) 1% HEC+1.5% Glycerol
  (d) 1% HEC+5% Trehalose
  (e) 1% HEC+5% Sucrose
  (f) 1% HEC+10% Trehalose
  (g) 1% HEC+10% Sucrose
  (h) 1% HEC+5% Trehalose+1.5% Glycerol
  (i) 1% HEC+5% Sucrose+1.5% Glycerol
  (j) 1% HEC+10% Trehalose+1.5% Glycerol
  (k) 1% HEC+10% Sucrose+1.5% Glycerol
  (l) 2% HEC+10% Sucrose
  (m) 2% HEC+10% Sucrose+1.5% Glycerol The cell mixtures were lyophilized as described in Table 3.

TABLE 3

| Process step | Step description |
|---|---|
| Loading | Incubate at 5° C. and one atmosphere for 60 min |
| Freezing | Ramp shelf to −45° C. at an average controlled rate of 5° C./min. Control shelf at target set point of −45° C. for 285 min. |
| Primary drying/ Secondary drying | Evacuate chamber, control at a target set point of 60 mTorr. |
| | (a) Ramp shelf to −30° C. at an average controlled rate of 0.2° C./min. Control shelf at target set point of −30° C. for 2850 min. |
| | (b) Ramp shelf to −22° C. at an average controlled rate of 0.2° C./min. Control shelf at target set point of −22° C. for 1080 min. |
| | (c) Ramp shelf to −10° C. at an average controlled rate of 0.2° C./min. Control shelf at target set point of −10° C. for 720 min. |
| | (d) Control chamber pressure at a target set point of 60 mTorr. Ramp shelf to 25° C. at controlled average rate of 0.2° C./min Control shelf at target set point for 720 min |

After drying, each dried cake was resuspended in 12 ml of $H_2O$

Following the protocol above produced the following observations:

(a) Lyophilization cakes were elegant, except using conditions of 1% HEC+1.5% glycerol, and 1% HEC+5% sucrose+1.5% glycerol.

(b) Solubility during reconstitution of the cake was good in the absence of any excipient and using conditions of 1% HEC+1.5% glycerol.

(c) Cake in absence of excipients (i.e., buffer used in place of excipients) or using conditions of 1% HEC+1.5% glycerol had undissolved particles after reconstituting the cake with water.

The viability of the resuspended cells was tested, with the results shown in Table 4.

TABLE 4

(% Viability)

Protective Agents

| Concentration w/v Before Lyophilization | Concentration w/v after Resuspension of Cake in 12 ml H$_2$O | Viability Before Lyophilization (cfu) | Viability After Lyophilization (cfu) | Viability Percentage |
|---|---|---|---|---|
| Resuspended Pellet (A) | Not applicable. | 126 × 10$^9$ | N/A | N/A |
|  |  | 148 × 10$^9$ | N/A | N/A |
|  |  | 92 × 10$^9$ | N/A | N/A |
|  | Average | 1.2 ± 0.2 × 10$^{11}$ | N/A | N/A |
| Resuspended Pellet (B) | Not applicable. | 80 × 10$^9$ | N/A | N/A |
|  |  | 76 × 10$^9$ | N/A | N/A |
|  |  | 74 × 10$^9$ | N/A | N/A |
|  | Average | 7.7 ± 0.2 × 10$^{10}$ | N/A | N/A |
| 0.8% HEC | 0.8% HEC | N/A | 76 × 10$^6$ | 5.43 |
|  |  | N/A | 80 × 10$^6$ | 5.71 |
|  |  | N/A | 82 × 10$^6$ | 5.86 |
|  | Average | 1.4 ± 0.1 × 10$^9$ | (7.9 ± 0.2) × 10$^7$ | 5.67 ± 0.13% |
| 0.8% HEC + 1.3% Glycerol | 0.8% HEC + 1.3% Glycerol | N/A | 6 × 10$^5$ | 0.04 |
|  |  | N/A | 8 × 10$^5$ | 0.06 |
|  |  | N/A | N/A | N/A |
|  | Average | 1.4 ± 0.1 × 10$^9$ | (7 ± 1.0) × 10$^5$ | 0.05 ± 0.01% |
| 0.8% HEC + 4.2% Trehalose | 0.8% HEC + 4.2% Trehalose | N/A | 22 × 10$^7$ | 15.7 |
|  |  | N/A | 42 × 10$^7$ | 30.0 |
|  |  | N/A | 34 × 10$^7$ | 24.3 |
|  | Average | 1.4 ± 0.1 × 10$^9$ | (3.3 ± 0.6) × 10$^8$ | 23.3 ± 4.1% |
| 0.8% HEC + 4.2% Sucrose | 0.8% HEC + 4.2% Sucrose | N/A | 140 × 10$^7$ | 100 |
|  |  | N/A | 148 × 10$^7$ | 100 |
|  |  | N/A | 120 × 10$^7$ | 85.7 |
|  | Average | 1.4 ± 0.1 × 10$^9$ | (1.4 ± 0.1) × 10$^9$ | 95.2 ± 4.8% |
| 0.8% HEC + 8.3% Trehalose | 0.8% HEC + 8.3% Trehalose | N/A | 20 × 10$^7$ | 14.3 |
|  |  | N/A | 14 × 10$^7$ | 10.0 |
|  |  | N/A | 22 × 10$^7$ | 15.7 |
|  | Average | 1.4 ± 0.1 × 10$^9$ | (1.9 ± 0.2) × 10$^8$ | 13.3 ± 1.7% |
| 0.8% HEC + 8.3% Sucrose | 0.8% HEC + 8.3% Sucrose | 128 × 10$^7$ | 112 × 10$^7$ | 87.5 |
|  |  | 146 × 10$^7$ | 128 × 10$^7$ | 87.6 |
|  |  | 150 × 10$^7$ | 148 × 10$^7$ | 98.7 |
|  | Average | 1.41 ± 0.1 × 10$^9$ | (1.3 ± 0.1) × 10$^9$ | 91.3 ± 3.7% |
| 0.8% HEC + 4.2% Trehalose + 1.3% Glycerol | 0.8% HEC + 4.2% Trehalose + 1.3% Glycerol | N/A | 36 × 10$^7$ | 25.7 |
|  |  | N/A | 48 × 10$^7$ | 34.3 |
|  |  | N/A | 64 × 10$^7$ | 45.7 |
|  | Average | 1.41 ± 0.1 × 10$^9$ | (4.9 ± 0.8) × 10$^8$ | 35.2 ± 5.8% |
| 0.8% HEC + 4.2% Sucrose + 1.3% Glycerol | 0.8% HEC + 4.2% Sucrose + 1.3% Glycerol | N/A | 142 × 10$^7$ | 100 |
|  |  | N/A | 128 × 10$^7$ | 91.4 |
|  |  | N/A | 120 × 10$^7$ | 85.1 |
|  | Average | 1.41 ± 0.1 × 10$^9$ | (1.3 ± 1.2) × 10$^9$ | 92.2 ± 7.8% |
| 0.8% HEC + 8.3% Trehalose + 1.3% Glycerol | 0.8% HEC + 8.3% Trehalose + 1.3% Glycerol | N/A | 78 × 10$^7$ | 55.3% |
|  |  | N/A | 78 × 10$^7$ | 55.3% |
|  |  | N/A | 98 × 10$^7$ | 69.5% |
|  | Average | 1.41 ± 0.1 × 10$^9$ | (8.5 ± 0.7) × 10$^8$ | 60.0 ± 4.7% |
| 0.8% HEC + 8.3% Sucrose + 1.3% Glycerol | 0.8% HEC + 8.3% Sucrose + 1.3% Glycerol | N/A | 82 × 10$^7$ | 58.1% |
|  |  | N/A | 122 × 10$^7$ | 86.5% |
|  |  | N/A | 138 × 10$^7$ | 97.9 |
|  | Average | 1. 41 ± 0.1 × 10$^9$ | (1.1 ± 0.2) × 10$^9$ | 80.8 ± 11.8% |
| 1.7% HEC + 8.3% Sucrose | 1.7% HEC + 8.3% Sucrose | 128 × 10$^7$ | 52 × 10$^7$ | 41.3% |
|  |  | 126 × 10$^7$ | 42 × 10$^7$ | 33.3% |
|  |  | 124 × 10$^7$ | 56 × 10$^7$ | 44.4% |
|  | Average | 1.26 ± 0.02 × 10$^9$ | (5.0 ± 0.4) × 10$^8$ | 39.7 ± 3.3% |
| 1.7% HEC + 8.3% Sucrose + 1.3% Glycerol | 1.7% HEC + 8.3% Sucrose + 1.3% Glycerol | 118 × 10$^7$ | 84 × 10$^7$ | 73.0% |
|  |  | 124 × 10$^7$ | 86 × 10$^7$ | 74.8% |
|  |  | 104 × 10$^7$ | 100 × 10$^7$ | 86.9% |
|  | Average | 1.15 ± 0.1 × 10$^9$ | (9.01 ± 0.5) × 10$^8$ | 78.2 ± 4.4% |

While not limiting the present invention to any particular minimum of viability, it is observed that, using these experimental conditions, 1% HEC+5% and/or 10% Sucrose, in the presence and absence of 1.5% Glycerol, gave >90% viability after lyophilization. Similarly, using conditions of 2% HEC+10% Sucrose+1.5% Glycerol allows for ~80% viability.

Example 3

Preparation of Freeze-Dried *E. coli* HU2117

Protocol 3

Cell Preparation

One 2 liter flask of cells was grown from 1 ml of seed stock inoculated into 1 L Modified EZ Rich Defined Glycerol medium, incubated at 37±1° C. for 8 hrs with constant shaking at 250 RPM. At the end of 8 hours, the $OD_{600}$ was 2.2±0.03.

The cells were collected by centrifugation at 4° C., at 6000 RPM for 8 min. The pelleted cells were washed twice with 0.9% saline and washed once with 10 mM citrate buffer, pH 7.0.

The pelleted cells were resuspended into 2-3 ml of 10 mM citrate buffer, pH 7.0, for a final volume of approximately 10 ml.

The concentration of the resuspended cells was determined using plate counts. The resuspended cells had a viable cell concentration of $4.9 \times 10^{10}$ CFU/ml.

Lyophilization

For each test, 0.5 ml of resuspended cells were mixed with 1.5 ml of an excipient selected from the list below and 10 ml of 2% autoclaved hydroxyethyl cellulose (HEC).

Excipients (shown as the concentration (w/v) that would be achieved if the dried cake is resuspended to a final volume of 10 ml; if a different volume of fluid is used for dissolving the cake, the concentrations vary proportionally):
(a) buffer
(b) 2% HEC
(c) 2% HEC+5% Sucrose
(d) 2% HEC+10% Sucrose (12 ml)
(e) 2% HEC+10% Sucrose (10 ml)
(f) 2% HEC+5% Sucrose+1.5% Glycerol
(g) 2% HEC+10% Sucrose+1.5% Glycerol The cell mixtures were lyophilized as described in Table 5.

TABLE 5

| Process step | Step description |
|---|---|
| Loading | Incubate at 5° C. and one atmosphere for 60 min |
| Freezing | Ramp shelf to −45° C. at an average controlled rate of 5° C./min. Control shelf at target set point of −45° C. for 285 min. |
| Primary drying/ Secondary drying | Evacuate chamber, control at a target set point of 60 mTorr.<br>(e) Ramp shelf to −30° C. at an average controlled rate of 0.2° C./min. Control shelf at target set point of −30° C. for 2850 min.<br>(f) Ramp shelf to −22° C. at an average controlled rate of 0.2° C./min. Control shelf at target set point of −22° C. for 1080 min.<br>(g) Ramp shelf to −10° C. at an average controlled rate of 0.2° C./min. Control shelf at target set point of −10° C. for 600 min.<br>(h) Control chamber pressure at a target set point of 60 mTorr. Ramp shelf to 25° C. at controlled average rate of 0.2° C./min Control shelf at target set point for 720 min |

After drying, each dried cake was resuspended in 12 ml $H_2O$, with the exception of (e) above that was resuspended in 10 ml $H_2O$.

Following the protocol above produced the following observations:
(a) Following lyophilization, the cake was elegant in using conditions of 2% HEC+10% sucrose±1.5% glycerol.
(b) Solubility during reconstitution of the cake was good in all cases, except for in the absence of excipients.
(c) The cake, produced in the absence of excipients (e.g., buffer used in place of excipients) or using conditions of 2% HEC+5% sucrose had undissolved particles after reconstitution with water.

The viability of the resuspended cells was tested, with the results shown in Table 6.

TABLE 6

| | | (% Viability) | | |
|---|---|---|---|---|
| | Protective agents | | | |
| Concentration w/v Before Lyophilization | Concentration w/v after Resuspension of Cake in 10 ml or 12 ml $H_2O$ | Viability Before Lyophilization (cfu/ml) | Viability After Lyophilization (cfu/ml) | Viability Percentage |
| Resuspended Pellet (A)/10 ml | Not applicable. | $4.9 \times 10^{10}$ | N/A | N/A |
| | | $2.0 \times 10^{10}$ | N/A | N/A |
| | Average | $3.45 \pm 1.45 \times 10^{10}$ | N/A | N/A |
| 1.7% HEC | 1.7% HEC | N/A | $2.8 \times 10^6$ | 0.2 |
| | | N/A | $3.0 \times 10^6$ | 0.2 |
| | Average | $1.4 \pm 0.1 \times 10^9$ | $(2.9 \pm 0.1) \times 10^6$ | $0.2 \pm 0.01\%$ |
| 1.7% HEC + 4.2% Sucrose | 1.7% HEC + 4.2% Sucrose | $4.6 \times 10^9$ | $1.33 \times 10^9$ | 46.7 |
| | | $2.6 \times 10^9$ | $1.6 \times 10^9$ | 56.1 |
| | | $1.35 \times 10^9$ | N/A | N/A |
| | Average | $2.85 \pm 0.9 \times 10^9$ | $(1.4 \pm 0.1) \times 10^9$ | $51.4 \pm 4.7\%$ |
| 1.7% HEC + 8.3% Sucrose | 1.7% HEC + 8.3% Sucrose | $4.5 \times 10^9$ | $1.45 \times 10^9$ | 37.7 |
| | | $3.2 \times 10^9$ | $8.00 \times 10^8$ | 20.8 |
| | Average | $3.85 \pm 0.6 \times 10^9$ | $(1.15 \pm 0.3) \times 10^9$ | $29.2 \pm 8.4\%$ |
| 1.7% HEC + 8.3% Sucrose | 2% HEC + 10% Sucrose | N/A | $2.61 \times 10^9$ | 67.8 |
| | | N/A | $2.50 \times 10^9$ | 64.9 |
| | Average | N/A | $2.55 \pm 0.1 \times 10^9$ | $66.3 \pm 1.5\%$ |
| 1.7% HEC + 4.2% Sucrose + 1.3% Glycerol | 1.7% HEC + 4.2% Sucrose + 1.3% Glycerol | N/A | $2.58 \times 10^9$ | 67.0 |
| | | N/A | $2.50 \times 10^9$ | 64.9 |
| | Average | N/A | $(2.54 \pm 0.04) \times 10^9$ | $65.9 \pm 1.0\%$ |
| 1.7% HEC + 8.3% Sucrose + 1.3% Glycerol | 1.7% HEC + 8.3% Sucrose + 1.3% Glycerol | N/A | $2.9 \times 10^9$ | 75.3 |
| | | N/A | $5.4 \times 10^9$ | 100% |
| | Average | N/A | $(4.15 \pm 1.25) \times 10^9$ | $87.6 \pm 12.4\%$ |

While not limiting the present invention to any particular minimum of viability, it is observed that, using these experimental conditions, 2% HEC+10% Sucrose+1.5% Glycerol allows for ~80% viability. Following reconstitution of the cakes and determination of viable cell counts, it was observed that resuspension of the cake in 12 ml H₂O (d) or in 10 ml H₂O (e) had no difference in effect on the viability.

Figure 1:
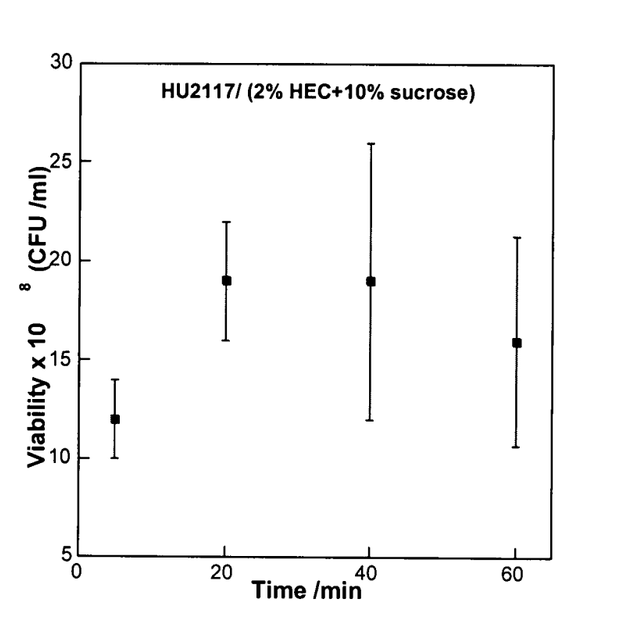
FIG. 1 shows a graphic representation of the effect of time after resuspension on microbes prepared according to the protocol described in Example 3.

Viability tests reported above in Examples 1-3 were conducted within about 30 minutes after resuspension. The viability of the cells in Example 3 was also tested at different time intervals (5, 20, 40, and 60 minutes) after resuspension. The effect of the time after resuspension is shown in FIG. 1.

The forgoing examples show that the probiotic microbes can be freeze-dried in the presence of a gelling agent, and reconstituted after drying to from a gel containing viable probiotic organisms. The methods and compositions provided herein provide for simplified delivery of probiotic organism, e.g., for use in preventing CAUTI.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A composition for preparing a medical lubricant gel, comprising a mixture of a) a probiotic microbe, b) a pharmaceutically acceptable gelling agent, and c) a pharmaceutically acceptable first protective agent, wherein said mixture is in freeze-dried form; wherein said gelling agent is hydroxyethyl cellulose; and wherein said protective agent is selected from the group consisting of non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride.

2. The composition of claim 1, further comprising a pharmaceutically acceptable second protective agent, wherein said second protective agent is different from said first protective agent, and is selected from the group consisting of non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride.

3. The composition of claim 1, wherein said probiotic microbe is a strain of E. coli.

4. The composition of claim 3, wherein said strain of E. coli is E. coli 83972.

5. The composition of claim 3, wherein said strain of E. coli is E. coli HU2117.

6. The composition of claim 1, wherein said first protective agent is sucrose.

7. The composition of claim 2, wherein said second protective agent different from said first protective agent, and is selected from the group consisting of non-fat milk solids, trehalose, glycerol, betaine, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride.

8. The composition of claim 1, wherein said composition is produced by a method comprising:

a) providing in an aqueous fluid a mixture comprising:
  i) said probiotic microbe;
  ii) said pharmaceutically acceptable gelling agent; and
  iii) said pharmaceutically acceptable first protective agent,
b) freeze-drying said mixture to produce a dried preparation.

9. The composition of claim 8, wherein said mixture further comprises a pharmaceutically acceptable second protective agent, wherein said second protective agent is different from said first protective agent, and is selected from the group consisting of non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride.

10. The composition of claim 8, wherein said probiotic microbe is a strain of E. coli.

11. The composition of claim 10, wherein said strain of E. coli is E. coli 83972.

12. The composition of claim 10, wherein said strain of E. coli is E. coli HU2117.

13. The composition of claim 8, wherein said first protective agent is sucrose.

14. The composition of claim 13, wherein said second protective agent different from said first protective agent, and is selected from the group consisting of non-fat milk solids, trehalose, glycerol, betaine, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride.

15. The composition of claim 2, wherein said mixture comprises:

a) a strain of E. coli selected from the group consisting or E. coli 83972 and E. coli HU2117;
b) sucrose; and
c) glycerol.

16. A method of administering a probiotic microbe to a subject, comprising:

a) providing a freeze-dried composition according to claim 1;
b) exposing said freeze dried composition to an aqueous fluid to form a gel comprising an effective amount of said probiotic microbe; and
c) contacting said subject with said gel.

17. The method of claim 16, wherein contacting said subject with said gel comprises contacting a medical device with said gel to produce a treated device, and contacting said subject with said treated device.

18. The method of claim 17, wherein said medical device is a urinary catheter.

19. The method of claim 16, wherein said probiotic microbe is E. coli HU2117 or E. coli 83972.

20. A kit comprising a composition comprising a freeze dried composition according to claim 1.

21. The kit of claim 20, wherein said composition further comprises a pharmaceutically acceptable second protective agent.

22. The kit of claim 20, further comprising a container of sterile aqueous fluid.

23. The kit of claim 20, wherein said probiotic microbe is a strain of E. coli.

24. The kit of claim 23, wherein said strain of E. coli is E. coli 83972.

25. The kit of claim 23, wherein said strain of E. coli is E. coli HU2117.

* * * * *